United States Patent
Lee et al.

(10) Patent No.: US 9,364,391 B2
(45) Date of Patent: Jun. 14, 2016

(54) APPARATUS FOR DISPLAYING ACUPUNCTURE POINTS

(75) Inventors: Sang Hun Lee, Daejeon (KR); Yeon Hee Ryu, Daejeon (KR); Sun Mi Choi, Daejeon (KR)

(73) Assignee: Korea Institute of Oriental Medicine, Daejeon (KR)

(*) Notice: Subject to any disclaimer, the term of this patent is extended or adjusted under 35 U.S.C. 154(b) by 342 days.

(21) Appl. No.: 13/640,961

(22) PCT Filed: Mar. 10, 2011

(86) PCT No.: PCT/KR2011/001656
§ 371 (c)(1),
(2), (4) Date: Oct. 12, 2012

(87) PCT Pub. No.: WO2011/129528
PCT Pub. Date: Oct. 20, 2011

(65) Prior Publication Data
US 2013/0027368 A1    Jan. 31, 2013

(30) Foreign Application Priority Data
Apr. 14, 2010 (KR) .......... 10-2010-0034254

(51) Int. Cl.
| A61H 39/02 | (2006.01) |
| A61H 39/00 | (2006.01) |
| A61N 5/06 | (2006.01) |
| A61B 5/107 | (2006.01) |
| A61B 5/053 | (2006.01) |

(52) U.S. Cl.
CPC ............... *A61H 39/02* (2013.01); *A61B 5/0532* (2013.01); *A61B 5/1079* (2013.01); *A61H 39/00* (2013.01);
(Continued)

(58) Field of Classification Search
CPC ... A61H 39/00; A61H 39/02; A61H 2230/85; A61B 5/0532; A61B 5/1079; Y10S 128/907; A61N 5/0619
USPC .......................................... 600/548; 606/189
See application file for complete search history.

(56) References Cited

U.S. PATENT DOCUMENTS

| 6,258,047 B1 * | 7/2001 | Muramatsu ............ A61B 5/103 600/594 |
| 7,076,293 B2 * | 7/2006 | Wang ................................. 607/2 |

(Continued)

FOREIGN PATENT DOCUMENTS

| JP | 2007-328004 A | 12/2007 |
| KR | 200418913 Y1 | 6/2006 |

(Continued)

OTHER PUBLICATIONS
International Search Report dated Nov. 21, 2011, as issued in International Application No. PCT/KR2011/001656, filed Mar. 10, 2011.

*Primary Examiner* — Devin Henson
(74) *Attorney, Agent, or Firm* — Maier & Maier, PLLC

(57) ABSTRACT

An apparatus for displaying acupuncture points according to the present invention recognizes a curved surface of a human body via 3D scanning, and then sets acupuncture points corresponding to the body surface that has been recognized to project them onto the body. More specifically, the apparatus for displaying acupuncture points comprises: a 3D scanner for performing 3D scanning; a control unit for setting acupuncture points by using the data that has been scanned by the 3D scanner; and a projection unit for projecting the acupuncture points that have been set by the control unit onto the body. Accordingly, the present invention allows accurate selection of acupuncture points on a highly curved surface of a human body.

5 Claims, 1 Drawing Sheet

(52) U.S. Cl.
CPC . *A61H 2201/1628* (2013.01); *A61H 2201/5043* (2013.01); *A61H 2201/5092* (2013.01); *A61H 2205/083* (2013.01); *A61H 2230/85* (2013.01); *A61H 2230/855* (2013.01); *A61N 5/0619* (2013.01); *Y10S 128/907* (2013.01)

(56) References Cited

U.S. PATENT DOCUMENTS

2001/0030754 A1* 10/2001 Spina et al. .................. 356/601
2007/0298396 A1* 12/2007 Wen ........................ G09B 23/28
                                                        434/262
2008/0312718 A1* 12/2008 Kulkarni et al. ................. 607/59

FOREIGN PATENT DOCUMENTS

| KR | 100767621 | B1 | | 10/2007 | |
|----|-----------|----|----|---------|---|
| KR | 1020090004250 | A | | 1/2009 | |
| KR | 10-2009-0020051 | | * | 2/2009 | ............ G06Q 50/00 |
| KR | 1020090045876 | A | | 5/2009 | |
| KR | 100919837 | B1 | | 10/2009 | |

* cited by examiner

APPARATUS FOR DISPLAYING ACUPUNCTURE POINTS

RELATED APPLICATIONS

This is the U.S. national stage application which claims priority under 35 U.S.C. §371 to International Patent Application No.: PCT/KR2011/001656, filed on Mar. 10, 2011, which claims priority to Korean Patent Application No. 10-2010-0034254, filed on Apr. 14, 2010, the disclosures of which are incorporated by reference herein their entireties.

BACKGROUND OF THE INVENTION

1. Technical Field

The present invention relates to an apparatus for displaying acupuncture points, capable of accurately determining acupuncture points on an uneven external body surface via three-dimensionally scanning.

2. Description of the Related Art

General apparatus for displaying acupuncture points recognize only an outline of a human body.

For example, when determining a navel and pubic bones as reference points to measure acupuncture points on lower abdomen, there are present a Qugu (a pubic bone, 曲骨, CV2), Zhongji (中極, CV3), Guanyuan (關元, CV4), Shimen (石門, CV5), Yinjiao (陰交, CV7), Shenque (a navel, 神闕, CV8) at every Cun between the navel and the pubic bones. In this case, when straightly projecting acupuncture points in front of an examinee without considering a curved surface of a human body, there occurs a serious distortion depending on a height of lower abdomen of the examinee.

Particularly, when a gradient of a pubic portion of a person with abdominal obesity is about 45° and projecting acupuncture points in front of the obese person, a display length between pubic bones and the Zhongji (中極, CV3) acupuncture point is distorted as about 1.4 Cun and it is impossible to display precision meridians, that is, the position of acupuncture points.

That is, general apparatuses employ simple plane information to determine acupuncture points, thereby distorting determined acupuncture points according to a curved surface of a human body, which causes imprecise determination.

SUMMARY OF THE INVENTION

According to an aspect of the present invention, there is provided an apparatus for displaying acupuncture points, the apparatus recognizing an uneven external body surface of a human body via three-dimensionally scanning, determining acupuncture points in response to the recognized external body surface, and projecting the acupuncture points to the human body.

In detail, the apparatus includes a three-dimensional scanner three-dimensionally scanning a human body; a control unit determining acupuncture points by using data formed via the scanning of the three-dimensional scanner; and a projection unit projecting the acupuncture points determined by the control unit to the human body.

In this case, the control unit may determine the acupuncture points by converting the locations proportionally, comparing the reference and the scanned 3D body surface.

Also, when there is a mark on a reference point obtained through perceiving by touch of an examiner, the control unit may be provided to recognize the mark and to adjust the acupuncture points previously determined based on the external body surface by using the three-dimensional scanner by using data of the recognized mark.

According to another aspect of the present invention, there is provided a method of using the apparatus for displaying acupuncture points, the method including: three-dimensionally scanning a human body; determining the acupuncture points by using data formed by the three-dimensionally scanning; and projecting the determined acupuncture points to the human body.

In the determining the acupuncture points, the acupuncture points may be determined by proportionally matching data with reference to an external body surface in the data scanned 3D by the three-dimensionally scanning.

Also, the method further includes, after the projecting the acupuncture points, when there is a mark on an acupuncture point obtained by perceiving by touch of an examiner, adjusting the previously determined acupuncture points by using data of the recognized mark; and projecting the adjusted acupuncture points to the human body.

The present invention provides an effect of accurately determining acupuncture points on an uneven external body surface of a human body, in which the uneven external body surface is recognized via three-dimensionally scanning, the acupuncture points are determined to correspond to the recognized external body surface, and the acupuncture points are projected to the human body.

DETAILED DESCRIPTION OF EXEMPLARY EMBODIMENTS

According to an embodiment of the present invention, an uneven external body surface of a human body is recognized and acupuncture points are determined corresponding to the recognized external body surface and projected to the human body.

Figure 1:
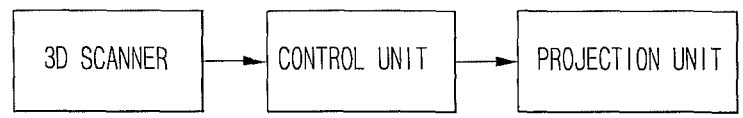
FIG. 1 is a block diagram illustrating an apparatus for displaying acupuncture points according to an embodiment of the present invention.

FIG. 1 is a block diagram illustrating an apparatus for displaying acupuncture points according to an embodiment of the present invention.

Referring to FIG. 1, the apparatus includes a three-dimensional scanner three-dimensionally scanning a human body, a control unit determining the acupuncture points via the three-dimensional scanner, and a projection unit projecting the determined acupuncture points to the human body.

The three-dimensional scanner allows that the same data as an actual shape may be obtained by three-dimensionally scanning an external body surface of an examinee, including uneven portions, when measuring acupuncture points of the examinee.

In addition, the three-dimensional scanner may automatically measure innumerable coordinates on the external body surface of the examinee at high speed and may form a three-dimensional model capable of being used to determine the acupuncture points on the external body surface of the examinee.

In this case, the three-dimensional scanner may be just a unit capable of displaying the external body surface of the examinee and a kind or a scanning method thereof is not limited in the present invention.

Also, the control unit determines the acupuncture points by using data formed by the scanning of the three-dimensional scanner. The control unit may be, for example, a unit such as a micro computer and determines the acupuncture points by proportionally matching data with reference to an external body surface in the data scanned 3D by the scanning.

On the other hand, the projection unit projects the acupuncture points determined by the control unit to the human body.

The projection unit may project and display the determined acupuncture points to the external body surface of a human by using appropriate means such as photo and a unit capable of projecting is not limited in the present invention.

On the other hand, the control unit may be provided to recognize a mark shown on the external body surface of the examinee.

When there is a mark on a reference point obtained by perceiving by touch of the examiner, the control unit may be provided to recognize the mark.

In this case, the control unit may be provided to adjust the acupuncture points previously determined based on the external body surface by the three-dimensional scanner by using data of the recognized mark.

For example, when a skilled examiner examines the examinee by perceiving by touch and designates a point capable of being a reference point on the external body surface, the control unit may sense, that is, recognize the mark used as a recognition element.

In this case, a detailed recognition method of the control unit may be not limited in the present invention, to which several methods may be applied.

Figure 2:
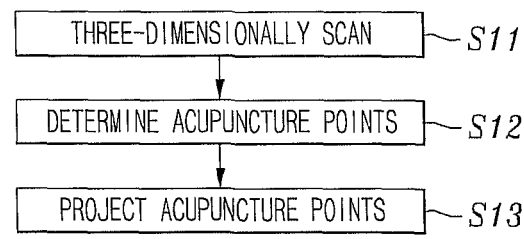
FIG. 2 is a flowchart illustrating a method of displaying acupuncture points according to an embodiment of the present invention.
Figure 3:
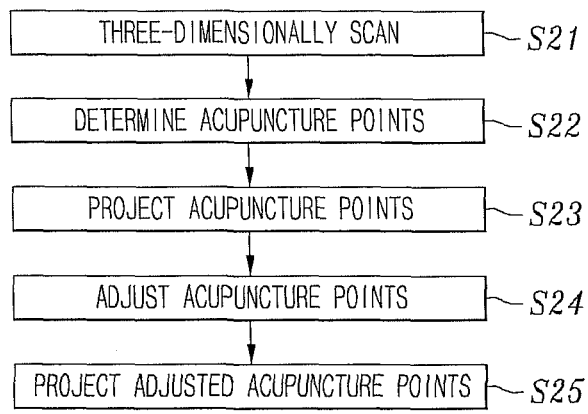
FIG. 3 is a flowchart illustrating a method of displaying acupuncture points according to another embodiment of the present invention.

FIG. 2 is a flowchart illustrating a method of displaying acupuncture points according to an embodiment of the present invention. FIG. 3 is a flowchart illustrating a method of displaying acupuncture points according to another embodiment of the present invention.

Referring to FIGS. 2 and 3, a human body of an examinee is three-dimensionally scanned (S11 and S21), in which a three-dimensional scanner is used for three-dimensionally modeling.

After that, acupuncture points may be determined by a control unit electrically connected to the three-dimensional scanner by using data formed by the three-dimensionally scanning (S12 and S22).

In this case, the acupuncture points may be determined by proportionally matching data with reference to an external body surface in the data scanned 3D.

Finally, the determined acupuncture points are projected to a human body, that is, to an external body surface of the examinee (S13 and S23). In other words, the determined acupuncture points may be displayed on the external body surface by using a projection unit in such a way that an examiner may recognize the acupuncture points.

In addition, after projecting the determined acupuncture points, when there is a mark obtained by perceiving by touch of the examiner and the acupuncture points previously determined are adjusted using data of the recognized mark (S24).

Furthermore, the adjusted acupuncture points may be projected to the external body surface of the examinee (S25).

While the present invention has been particularly shown and described with reference to exemplary embodiments thereof, it will be understood by those skilled in the art that various changes in form and details may be made therein without departing from the spirit and scope of the invention as defined by the appended claims.

What is claimed is:

1. A method for displaying acupuncture points, comprising:
    scanning an external, uneven surface of a human body with a three-dimensional scanner;
    forming a three-dimensional model of the external, uneven surface with data obtained by the three-dimensional scanner;
    determining, with a control unit, acupuncture points corresponding to the external, uneven surface by comparing the data obtained by the scanner with known acupuncture reference points;
    converting, with the control unit, the scanned acupuncture points to proportionally correspond with the known acupuncture reference points on the external, uneven surface;
    projecting, with a projection device, the acupuncture points determined and converted by the control unit on to the external, uneven surface of the human body and;
    using the projected acupuncture points as sites for acupuncture.

2. An apparatus for displaying acupuncture points, the apparatus comprising:
    a three-dimensional scanner for three-dimensionally scanning a human body with an uneven surface;
    a three-dimensional model of the human body formed with data generated by the three-dimensional scanner;
    a control unit for determining acupuncture points corresponding to the human body by comparing the data obtained-by the scanner with known acupuncture reference points and proportionally converting, the scanned acupuncture points to correspond with the known acupuncture reference points on the uneven body surface; and
    a projection unit for projecting the acupuncture points determined by the control unit on to the human body.

3. The apparatus of claim 2, wherein the control unit is operable to identify a manually-determined reference point by recognizing a predetermined mark and adjusts the previously determined acupuncture points based on the recognized mark.

4. A method of displaying acupuncture points, the method comprising:
    scanning a human body with an uneven surface with a three-dimensional scanner;
    determining acupuncture points with a control unit by comparing the data obtained by the three-dimensional scan with of known acupuncture reference points to determine acupuncture points on the human body;
    converting, with the control unit, the scanned acupuncture points to proportionally correspond with the known acupuncture reference points on the uneven body surface; and
    projecting the determined acupuncture points on the human body with a projection device.

5. The method of claim 4, further comprising:
    identifying, with the control unit, a manually-determined reference point by recognizing a predetermined mark;
    adjusting the previously determined acupuncture points by using data of the recognized mark; and
    projecting the adjusted acupuncture points to the human body.

* * * * *